(12) United States Patent
Bobylev

(10) Patent No.: US 8,710,268 B2
(45) Date of Patent: *Apr. 29, 2014

(54) METHOD FOR THE HYDROLYSIS OF SUBSTITUTED FORMYLAMINES INTO SUBSTITUTED AMINES

(71) Applicant: Mikhail Bobylev, Minot, ND (US)

(72) Inventor: Mikhail Bobylev, Minot, ND (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/657,505

(22) Filed: Oct. 22, 2012

(65) Prior Publication Data

US 2013/0046111 A1    Feb. 21, 2013

Related U.S. Application Data

(63) Continuation of application No. 12/182,451, filed on Jul. 30, 2008, now Pat. No. 8,329,948.

(60) Provisional application No. 60/962,739, filed on Jul. 31, 2007.

(51) Int. Cl.
*C07C 209/62* (2006.01)

(52) U.S. Cl.
USPC .......................................... 564/386

(58) Field of Classification Search
USPC .................................................. 564/336, 386
See application file for complete search history.

(56) References Cited

U.S. PATENT DOCUMENTS 8,329,948 B2 * 12/2012 Bobylev ....................... 564/215

FOREIGN PATENT DOCUMENTS

EP        0 518 414    * 12/1992

* cited by examiner

*Primary Examiner* — Shailendra Kumar
(74) *Attorney, Agent, or Firm* — James K Petell

(57) ABSTRACT

An improved method for the synthesis of substituted formylamines and substituted amines via an accelerated Leuckart reaction. The Leuckart reaction is accelerated by reacting formamide or N-alkylformamide and formic acid with an aldehyde or a ketone at a preferred molar ratio that accelerates the reaction. The improved method is applicable to various substituted aldehydes and ketones, including substituted benzaldehydes. An accelerated method for the hydrolysis of substituted formylamines into substituted amines using acid or base and a solvent at an elevated temperature. The improved method is useful for the accelerated synthesis of agrochemicals and pharmaceuticals such as vanillylamine, amphetamine and its analogs, and formamide fungicides.

9 Claims, No Drawings

METHOD FOR THE HYDROLYSIS OF SUBSTITUTED FORMYLAMINES INTO SUBSTITUTED AMINES

CROSS-REFERENCE TO RELATED APPLICATION

This application is a continuation application of the prior application Ser. No. 12/182,451 filed Jul. 30, 2008, now U.S. Pat. No. 8,329,948, which claims the benefit to U.S. Provisional Patent Application Serial No. 60/962,739 filed Jul. 31, 2007, which are hereby incorporated herein by reference in their entirely.

BACKGROUND OF THE INVENTION

Aldehydes and ketones are valuable building blocks for chemical industry. Reductive amination is a fundamental chemistry process that dramatically expands the application of aldehydes and ketones by transforming them into amines. The Leuckart reaction is a unique one step method of reductive amination. It is a remarkably simple process that includes only two components: the carbonyl compound and formamide. The reaction is completed simply by heating the components at 160° C. to 185° C. for 6 to 25 hours [1]. The long processing time seemed to be the only shortcoming of the reaction. However, it is associated with a number of serious practical problems.

First, the prolonged exposure of the reaction mixture to high temperatures inevitably leads to significant thermal decomposition of the components, and, consequently, to lower yields of the products and difficulties with their isolation and purification. Second, maintaining high temperatures for a long period of time means high consumption of energy and increasing production costs which make the Leuckart reaction unattractive to chemical industry. Third, long processing times per se are unattractive to fast paced modern synthetic applications, such as combinatorial chemistry and automated parallel synthesis. Thus, the Leuckart reaction as a unique one step method of reductive amination became almost completely abandoned in modern synthetic chemistry.

Most of the current reductive amination procedures are currently performed as two step combinations of the separate amination and reduction reactions. These two step procedures can often take as much time as the traditional Leuckart reaction [2]. They are also quite expensive because they require either the use of custom complex hydrides, or precious metal catalysts and high pressure equipment. Their only advantage over the one step Leuckart reaction is that they are not accompanied by thermal decomposition and as a result produce cleaner products.

Therefore, it is evident that there is a compelling need for a fast and inexpensive method of reductive amination of aldehydes and ketones equally attractive to industrial and laboratory practices.

SUMMARY OF THE INVENTION

An improved method for the synthesis of substituted formylamines via an accelerated Leuckart reaction. The method may also include an accelerated hydrolysis of the substituted formylamines to substituted amines. The accelerated Leuckart reaction is conducted by reacting formamide or N-alkylformamide, formic acid and an aldehyde or a ketone at a specific molar ratio and a specific temperature. The accelerated Leuckart reaction is completed within minutes or seconds instead of hours. The accelerated hydrolysis is conducted in the presence of a specific acid and a specific solvent at an elevated temperature. The accelerated hydrolysis is also completed within seconds.

DETAILED DESCRIPTION OF INVENTION

The improved method of reductive amination of aldehydes and ketones via an accelerated Leuckart reaction is an unanticipated discovery. The Leuckart reaction was first described in the XIX century, and since that time remained one of the slowest reactions in organic chemistry. Many attempts were made to improve the reaction by using various additives, most commonly formic acid. However, the only area of improvement appeared to be the yield of the product, not the processing time.

In 1996 a significantly shorter reaction time of 30 minutes was achieved through the use of microwave heating [3]. However, the technique was successfully applied only to a very narrow group of compounds. In addition, the current technical solutions for microwave assisted synthesis do not allow for processing large-scale reactions and therefore cannot be used in industry.

In the present invention using the Leuckart reaction it was unexpectedly discovered that the reaction time can be dramatically decreased by decreasing the concentration of the aldehyde or a ketone used in the reaction. Certain specific molar ratios of the aldehyde (ketone), formic acid, and formamide (alkylformamide) the reaction time can be reduced to 30 minutes or lower without the use of microwave assistance. Surprisingly it was found, that in many cases the reaction becomes instant, i.e. fully completed at the moment when it reaches the usual reaction temperature of 160-185° C. The accelerated Leuckart reaction is equally successful if it is conducted with conventional or microwave heating.

The unique molar ratio of formamide (N-alkylformamide) to an aldehyde or a ketone is between 150:1 to 5:1 and most preferably between 100:1 to 10:1. The specific molar ratio of formamide (N-alkylformamide) to formic acid is between 20:1 to 6:1 and most preferably 10:1.

The specific temperature of the accelerated Leuckart reaction is between 150-200° C., and most preferably 180-190° C., if the reaction is conducted in an open system. It was found that the specific temperature of the accelerated Leuckart reaction is between 150 to 250° C., most preferably 190-210° C., if the reaction is conducted in a sealed system.

This accelerated Leuckart reaction can be successfully applied to the areas where the traditional Leuckart reaction was not successful. Specifically, it was believed that the Leuckart reaction does not work on substituted benzaldehydes, and that the substituted benzylamines cannot be obtained from the respective benzaldehydes via the Leuckart reaction [1]. Further the accelerated Leuckart reaction does work on substituted benzaldehydes and that practically any substituted benzylamine can be prepared via the accelerated Leuckart reaction. Specifically, it was found that the reductive amination of vanillin (4-hydroxy-3-methoxybenzaldehyde) can be completed instantly via the accelerated Leuckart reaction. Vanillylamine is an important industrial chemical that is used for the synthesis of safe natural painkillers, such as capsaicin and analogs. The new accelerated Leuckart reaction comprises the new method of the synthesis of vanillylamine. Further, it was also discovered that the accelerated Leuckart reaction can be successfully applied to α,β-unsaturated aldehydes and ketones, thus comprising a new method of obtaining substituted allylamines.

The improved increased reaction rate prevents any substantial thermal deterioration of the reaction mixture. As a result, the filtrates obtained after the separation of the reaction products can be repeatedly used as solvents for the next rounds of the reaction. The accelerated Leuckart reaction allows for the recycling of the reaction filtrates thus leading to quantitative yields of the products and minimal amounts of wastes.

As a complementary process, it was shown that substituted formylamines that are obtained as a result of the Leuckart reaction can be hydrolyzed to substituted amines via an accelerated (instant) hydrolysis. Normally, the hydrolysis step that follows the Leuckart reaction is a relatively slow step that takes about an hour. Surprisingly, in the presence of a specific solvent the hydrolysis step also becomes an instant procedure. As a result, the entire process of obtaining amines from aldehydes and ketones becomes a combination of two accelerated (instant) reactions, an accelerated (instant) Leuckart reaction and accelerated (instant) hydrolysis.

The present invention is illustrated by the following examples herein.

EXAMPLE 1

Reductive amination of vanillin (I)

The multi-mode MARS 5 reaction system (CEM Corporation) with GreenChem reaction vessels was used for the synthesis of vanillylformamide (II). 1.52 g (10 mmol) of I, 20 ml of formamide, and 1 ml of formic acid were placed in the GreenChem reaction vessel. The GreenChem reaction vessel was placed into the MARS 5 reaction system and the reaction mixture was quickly heated to 200° C. The reaction mixture was kept at 200° C. for 3 minutes and then cooled to 100° C. The GreenChem reaction vessel was removed from the MARS 5 system, the residual pressure was released, and the reaction vessel was opened. TLC showed that the reaction was complete. The reaction mixture was diluted with 50 ml of water and extracted with ethyl acetate. The extract was dried with sodium sulfate and the solvent was evaporated. The residue was purified by column chromatography (silica gel, $CH_2Cl_2:CH_3OH$ 20:1 v/v) and yielded 1.37 g (75%) of N-vanillylformamide (II), m.p. 83.5° C. (benzene). $^1H$ NMR ($D_6$-acetone): 8.21 s (1H, HC=O), 7.60 s (1H, NH), 7.55 br.s. (1H, OH), 6.93 s (1H, aromatic), 6.76 s (2H, aromatic), 4.32 d (2H, $CH_2$), 3.80 s (3H, $CH_3$). $^{13}C$ NMR ($D_6$-acetone): 161.9 (C=O), 148.7, 147.1, 131.7, 121.6, 116.1, 112.6 (aromatic carbons), 56.6 ($CH_3$), 42.3 ($CH_2$). IR (neat crystals, ATR, $cm^{-1}$): 3296 (NH), 3213 (OH), 1643 (C=O). $C_9H_{11}NO_3$, calculated, %: C, 59.66; H, 6.12; N, 7.73. Found, %: C, 59.90, 59.89; H, 6.13, 6.12; N, 7.74, 7.73.

The reaction was repeated with 4.56 g (30 mmol) of vanillin and a reaction time of 1 min. TLC showed that the reaction was complete. The reaction mixture was extracted and purified the same way producing 3.29 g (60%) of N-vanillylformamide (II).

The reaction was repeated with 1.52 g (10 mmol) of vanillin and conventional heating at 190° C. for 1 minute. The reaction mixture was extracted and purified the same way producing 1.46 g (80%) of N-vanillylformamide (II).

EXAMPLE 2

Instant reductive amination of 4-hydroxybenzaldehyde (III)

4-hydroxybenzaldehyde (1.22 g or 10 mmol), formamide (22.72 g or 20.03 mL) and formic acid (2.43 g or 2 mL) were placed into a 50 mL round bottom flask equipped with a thermometer, a reflux condenser, a magnetic stirrer and a heating mantle. The reaction mixture was heated to 189° C. The heating was immediately turned off; the reaction flask was quickly raised from the heating mantle and allowed to cool to room temperature. The TLC conducted on the cold reaction mixture confirmed that the reaction was complete. The reaction mixture was diluted with 50 ml of water and extracted with ethyl acetate. The extract was dried with sodium sulfate and the solvent was evaporated to produce 1.17 g (77.1%) of 4-hydroxybenzylformamide (IV).

EXAMPLE 3

Reductive amination of 1-(2,4-dichlorophenyl)-4,4-dimethyl-1-propen-3-one (V)

One g (3.9 mmol) of V, 2 ml of formic acid, and 20 ml of formamide were placed in a round bottom flask equipped with thermometer, reflux condenser, and a heating mantle. The reaction mixture was heated to 188-190° C. and maintained at this temperature for 10 minutes. The reaction mixture was left to cool to room temperature overnight. The precipitated crystals were separated by filtration, rinsed with water, and dried with vacuum, producing 70% of N-[1-(2,4-dichlorophenyl)-4,4-dimethyl-1-propen-3-yl]-formamide (VI).

EXAMPLE 4

Reductive amination of benzophenone (VII)

The reaction procedure for V was repeated with 5 g of benzophenone and the reaction time of 15 minutes. The reaction produced 95% of benzhydrylformamide (VIII) (isolated yield).

EXAMPLE 5

Instant hydrolysis of N-[1-(2,4-dichlorophenyl)-4,4-dimethyl-1-propen-3-yl]formamide (VI)

One g of VI, 10 ml of concentrated hydrochloric acid, and 10 ml of methanol were placed in the GreenChem reaction vessel. The GreenChem reaction vessel was placed into the MARS 5 reaction system and the reaction mixture was quickly heated to 120° C. The microwave heating was immediately turned off and the reaction mixture was quickly cooled to 60° C. The GreenChem reaction vessel was removed from the MARS 5 system, the residual pressure was released, and the reaction vessel was opened. TLC showed that the reaction was complete. The reaction mixture was cooled to room temperature; the precipitated crystals were separated by filtration. The filtrate was dried with vacuum and produced an additional amount of the product. The yield of N-[1-(2,4-dichlorophenyl)-4,4-dimethyl-1-propen-3-yl]-amine hydrochloride (IX) is quantitative.

EXAMPLE 6

Instant hydrolysis of benzhydrylformamide (VIII)

The reaction procedure for VI was repeated with 1 g of VIII and produced quantitative yield of benzhydrylamine hydrochloride (X).

EXAMPLE 7

Instant hydrolysis of vanillylformamide (II)

The reaction procedure for VI was repeated with 1 g of II and produced quantitative yield of vanillylamine hydrochloride (XI).

EXAMPLE 8

Reductive amination of 2,4,6-trimethoxybenzaldehyde (XII) with recycling of the filtrate 1.96 g (10 mmol) of XII, 20 ml of formamide, and 2 ml of formic acid were placed in the GreenChem reaction vessel. The GreenChem reaction vessel was placed into the MARS-5 reaction system and the reaction mixture was quickly heated to 200° C. The reaction mixture was kept at 200° C. for 3 minutes and then cooled to 100° C. The GreenChem reaction vessel was removed from the MARS 5 system, the residual pressure was released, and the reaction vessel was opened. TLC showed that the reaction was complete. The reaction mixture was cooled to room temperature; the precipitated crystals were separated by filtration, rinsed with water and dried with vacuum. The filtrate was used as solvent in the next reaction. The reaction was repeated 10 times. The total of 9.6492 g of formic acid, and 34.5680 g of formamide were added to the reaction mixture over the ten cycles to compensate the losses. The total yield of 2,4,6-trimethoxybenzylformamide (XIII) is quantitative.

Other Embodiments

The description of the specific embodiments of the invention is presented for the purpose of illustration. It is not intended to be exhaustive nor to limit the scope of the invention to the specific forms described herein. Although the invention has been described with reference to several embodiments, it will be understood by one of ordinary skill in the art that various modifications can be made without departing from the spirit and the scope of the invention, as set forth in the claims. All patents, patent applications and publications referenced herein are hereby incorporated by reference.

Other embodiments are within the claims.

The invention claimed is:

1. A method for the accelerated hydrolysis of the substituted formylamine into a substituted amine, comprising:
   a. mixing the substituted formylamine with a volume of acid or base and alcohol in sealed reaction system;
   b. raising the temperature of the reaction mixture to a reaction temperature system between 100° C. and 160° C.; and
   c. maintaining the mixture to react at the reaction temperature for a time between 0 seconds to 60 minutes.

2. The method of claim 1; wherein the acid is hydrochloric acid.

3. The method of claim 1; wherein the base is sodium hydroxide.

4. The method of claim 1, wherein the reaction temperature is raised or maintained by conventional heating or by microwave heating.

5. The method of claim 1, further comprising cooling the mixture to room temperature and removing precipitated crystals by filtration.

6. The method of claim 1; wherein the substituted amine is a substituted allylamine, amphetamine or substituted amphetamine.

7. The method of claim 6, wherein the substituted amphetamine includes N-methylamphetamine, m-trifluoromethylamphetamine, and N-ethyl-m-trifluoromethylamphetamine.

8. The method of claim 1, wherein the substituted formylamine is a substituted allylformamide, N-formylamphetamine and substituted N-formylamphetamine.

9. The method of 1, wherein once the reaction temperature is reached, the heat is turned off.

* * * * *